United States Patent
DiMarzio et al.

(10) Patent No.: US 6,184,528 B1
(45) Date of Patent: Feb. 6, 2001

(54) METHOD OF SPECTRAL NONDESTRUCTIVE EVALUATION

(75) Inventors: Don DiMarzio, Northport; Louis Gregory Casagrande, Malvern; James A. Clarke, Greenlawn; Robert P. Silberstein, New York, all of NY (US)

(73) Assignee: Vought Aircraft Industries, Inc., Dallas, TX (US)

( * ) Notice: Under 35 U.S.C. 154(b), the term of this patent shall be extended for 0 days.

(21) Appl. No.: 09/140,986

(22) Filed: Aug. 27, 1998

(51) Int. Cl.⁷ ............................. G01N 21/47; G01N 21/55
(52) U.S. Cl. ............................. 250/339.08; 250/339.07; 250/339.09
(58) Field of Search ..................... 250/339.08, 339.09, 250/339.07

(56) References Cited

U.S. PATENT DOCUMENTS

| | | | |
|---|---|---|---|
| Re. 34,492 | 12/1993 | Roberts | 359/48 |
| 1,979,952 | 11/1934 | Benford | 88/23 |
| 3,720,806 | 3/1973 | Fotland | 219/216 |
| 3,808,439 | 4/1974 | Renius | 250/334 |
| 4,040,750 | 8/1977 | Zwiener | 356/212 |
| 4,109,508 | 8/1978 | Fukuyama | 73/15 |
| 4,135,232 | 1/1979 | Berkenhoff | 362/306 |
| 4,360,275 | 11/1982 | Louderback | 356/446 |
| 4,412,746 | 11/1983 | Yokouchi | 356/446 |
| 4,429,225 | 1/1984 | Fumoto et al. | 250/353 |
| 4,468,136 | 8/1984 | Murphy et al. | 374/45 |
| 4,487,504 | 12/1984 | Goldsmith | 356/323 |
| 4,547,073 | 10/1985 | Kugimiya | 356/371 |
| 4,551,628 | 11/1985 | Grossman | 250/503.1 |
| 4,555,635 | 11/1985 | Yoshida | 250/572 |
| 4,588,295 | 5/1986 | Elderinget et al. | 356/300 |
| 4,602,160 | 7/1986 | Mactaggart | 250/341 |
| 4,647,220 | 3/1987 | Adams et al. | 374/5 |
| 4,655,225 | 4/1987 | Dahne et al. | 128/633 |
| 4,667,112 | 5/1987 | Grossman | 250/503.1 |
| 4,673,818 | 6/1987 | Guerra | 250/571 |
| 4,740,708 | 4/1988 | Batchelder | 250/563 |
| 4,752,689 | * 6/1988 | Satake | 250/339.07 |

(List continued on next page.)

Primary Examiner—Constantine Hannaher
Assistant Examiner—Otilia Gabor
(74) Attorney, Agent, or Firm—Stetina Brunda Garred & Brucker

(57) ABSTRACT

In accordance with the present invention, there is provided a spectral nondestructive method for evaluating substrate surface characteristics of a sample substrate. The sample substrate has a sample substrate surface and a generally visually nontransmissive sample coating disposed on the sample substrate surface. The sample coating is transmissive within a first infrared spectral wavelength range and the sample substrate is reflective within the first infrared spectral wavelength range. The method begins with directing infrared radiation from an infrared radiation source towards the coated sample substrate. Specular and diffuse infrared radiation reflected from the coated sample substrate is collected. The reflected radiation is measured as a function of wavelength in the first infrared spectral wavelength range to obtain measured reflectance data representative of the reflectance of the coated sample substrate. The measured reflectance data is compared to reference reflectance data representative of a sample substrate surface having a known physical characteristic within the first wavelength range to obtain differential data. The differential data is correlated to physical characteristics of the sample substrate surface.

23 Claims, 3 Drawing Sheets

U.S. PATENT DOCUMENTS

| | | | |
|---|---|---|---|
| 4,809,147 | 2/1989 | Negishi | 362/347 |
| 4,854,724 | 8/1989 | Adams et al. | 374/5 |
| 4,859,062 | 8/1989 | Thurn et al. | 356/371 |
| 4,883,963 | 11/1989 | Kemeny et al. | 250/339 |
| 4,886,370 | 12/1989 | Koshihara et al. | 374/5 |
| 4,950,059 | 8/1990 | Roberts | 350/345 |
| 4,954,722 | 9/1990 | Fine et al. | 250/571 |
| 4,965,663 | 10/1990 | Sasaki | 358/80 |
| 4,974,138 | 11/1990 | Negishi | 362/347 |
| 4,983,836 | 1/1991 | Matoba et al. | 250/330 |
| 4,985,622 | 1/1991 | Kessler et al. | 250/226 |
| 4,988,205 | 1/1991 | Snail | 356/446 |
| 5,015,100 | 5/1991 | Doyle | 356/445 |
| 5,098,195 * | 3/1992 | Halyo et al. | 374/9 |
| 5,196,906 | 3/1993 | Stover et al. | 356/446 |
| 5,209,567 | 5/1993 | Loosen et al. | 374/32 |
| 5,239,269 | 8/1993 | Martens et al. | 324/632 |
| 5,241,369 | 8/1993 | McNeil et al. | 356/445 |
| 5,258,363 | 11/1993 | Hed | 505/1 |
| 5,294,198 | 3/1994 | Schlagheck | 374/5 |
| 5,321,970 * | 6/1994 | Davies et al. | 250/252.1 |
| 5,344,236 | 9/1994 | Fishman | 374/5 |
| 5,376,793 | 12/1994 | Lesniak | 250/341.8 |
| 5,422,483 | 6/1995 | Ando et al. | 250/330.02 |
| 5,440,238 | 8/1995 | Martens et al. | 324/636 |
| 5,475,220 * | 12/1995 | Hughes et al. | 250/339.09 |
| 5,490,161 | 2/1996 | Tanuma | 372/72 |
| 5,517,315 | 5/1996 | Snail et al. | 356/445 |
| 5,532,486 | 7/1996 | Ishibashi et al. | 250/341.3 |
| 5,537,203 | 7/1996 | Carr | 356/236 |
| 5,548,120 | 8/1996 | Parker et al. | 250/341.7 |
| 5,597,237 | 1/1997 | Stein | 374/9 |
| 5,668,887 | 9/1997 | Parker et al. | 382/108 |
| 5,714,758 * | 2/1998 | Neu | 250/339.08 |
| 5,719,395 | 2/1998 | Lesniak | 250/330 |
| 5,745,234 | 4/1998 | Snail et al. | 356/236 |
| 5,751,418 | 5/1998 | Kimura et al. | 356/319 |
| 5,793,042 * | 12/1998 | Quick | 250/339.08 |

* cited by examiner

METHOD OF SPECTRAL NONDESTRUCTIVE EVALUATION

FIELD OF THE INVENTION

The present invention relates generally to methods of evaluating substrate surface conditions of a coated substrate, and more particularly to a method of collecting and comparing infrared reflectance signatures within a spectral wavelength range of substrates having coatings having a non-zero transmittance within spectral wavelength range.

BACKGROUND OF THE INVENTION

Scatterometers provide a simple, nondestructive monitoring and evaluation technique to determine the surface microstructure of a sample. Generally, a scatterometer facilitates measurement of the directional energy distribution of radiation reflected from a sample surface. For example, if the sample surface is perfectly mat then the reflected radiation is diffuse, i.e., equal in all directions, whereas if the sample surface is not perfectly mat then the reflected radiation has a specular component, i.e., more concentrated in certain directions. This technique is useful in many areas of technology where observation of surface characteristics is evaluated.

Substrate materials having visually opaque coatings are often subject to physical/chemical changes. For example, substrate material may be susceptible to corrosion or heat damage which alter the substrate surface characteristic. The substrate coating, however, prevents a simple visual inspection of the nature of the underlying substrate surface.

It is therefore evident that there exists a need in the art for a method to evaluate substrate surface conditions of coated substrates where such method is nondestructive and is relatively simple to perform.

SUMMARY OF THE INVENTION

In accordance with the present invention, there is provided a spectral nondestructive method for evaluating substrate surface characteristics of a sample substrate. The sample substrate has a sample substrate surface and a generally visually nontransmissive sample coating disposed on the sample substrate surface. The sample coating is transmissive within a first infrared spectral wavelength range and the sample substrate is reflective within the first infrared spectral wavelength range. The method begins with directing infrared radiation from an infrared radiation source towards the coated sample substrate. Specular and diffuse infrared radiation reflected from the coated sample substrate is collected. The reflected radiation is measured as a function of wavelength in the first infrared spectral wavelength range to obtain measured reflectance data representative of the reflectance of the coated sample substrate. The measured reflectance data is compared to reference reflectance data representative of a sample substrate surface having a known physical characteristic within the first wavelength range to obtain differential data. The differential data is correlated to physical characteristics of the sample substrate surface.

In the preferred embodiment of the present invention, the first infrared spectral wavelength range is from 2 to 7 microns. The collection of the reflected infrared radiation may be facilitated by the use of an integrating sphere. In addition, a portable Fourier transform infrared spectrometer may be used to measure the reflectance of the coated sample. The reference reflectance data is representative of a coated reference substrate which is formed of similar material as that of the sample substrate and coating. Additional data may be collected and measured in a second infrared spectral wavelength range to account for differences in the reflectance characteristics of the sample coating in comparison the reference coating. In addition, the physical characteristics may correspond to corrosion or heat damage.

In another embodiment of the present invention, the reflectance of the sample substrate surface is calculated within the first infrared spectral wavelength range using the measured reflectance data to obtain measured substrate data. Such measured substrate data is compared with reference substrate data within the first infrared spectral wavelength range. The reference substrate data may be representative of a reference substrate formed of similar material as that of the sample substrate.

As such, based on the foregoing, the present invention mitigates the inefficiencies and limitations associated with prior art methods evaluating substrate surface conditions. The present invention is particularly adapted to facilitate evaluation and testing of subsurface characteristics of coated substrates. For example, a painted metal substrate is susceptible to corrosion (e.g., rust). It is recognized that corrosion changes the substrate surface reflectance characteristics. While the paint prevents light transmission in the visible range, the present method facilitates inspection substrate surface through the paint within a first infrared spectral wavelength range (i.e., an infrared evaluation window).

Importantly, the present method is nondestructive and non-contacting. In this respect, the method is purely spectral in nature and does not alter the physical integrity of the sample being evaluated. Advantageously, the present method may utilize commercially available devices, e.g., integrating spheres and Fourier transform infrared spectrometers.

Accordingly, the present invention represents a significant advance in the art.

BRIEF DESCRIPTION OF THE DRAWINGS

These, as well as other features of the present invention, will become more apparent upon reference to the drawings wherein.

DETAILED DESCRIPTION OF THE PREFERRED EMBODIMENT

Figure 1:
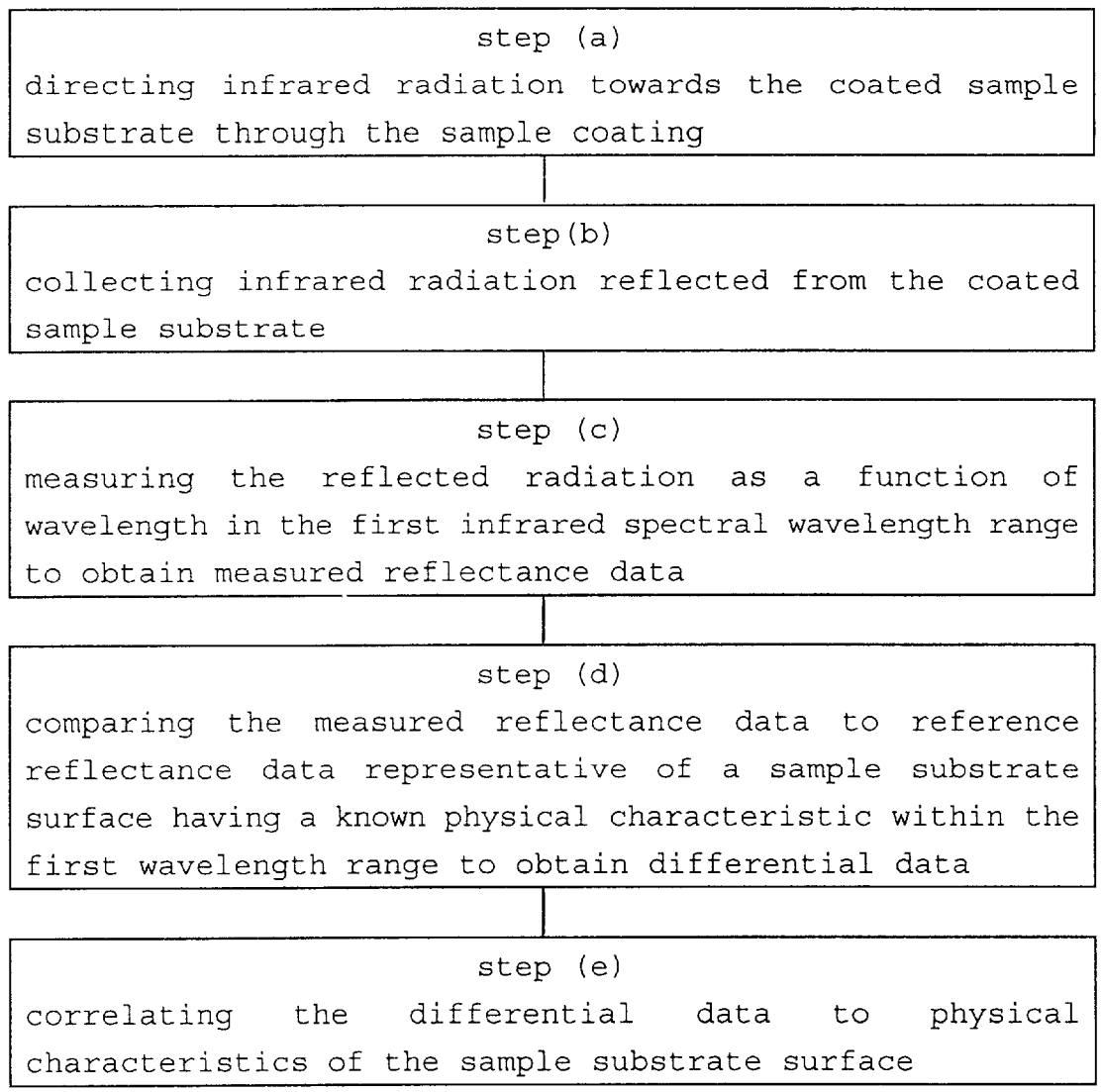
FIG. 1 is a flow chart of the method evaluating surface characteristics of a coated substrate of the present invention.
Figure 2:
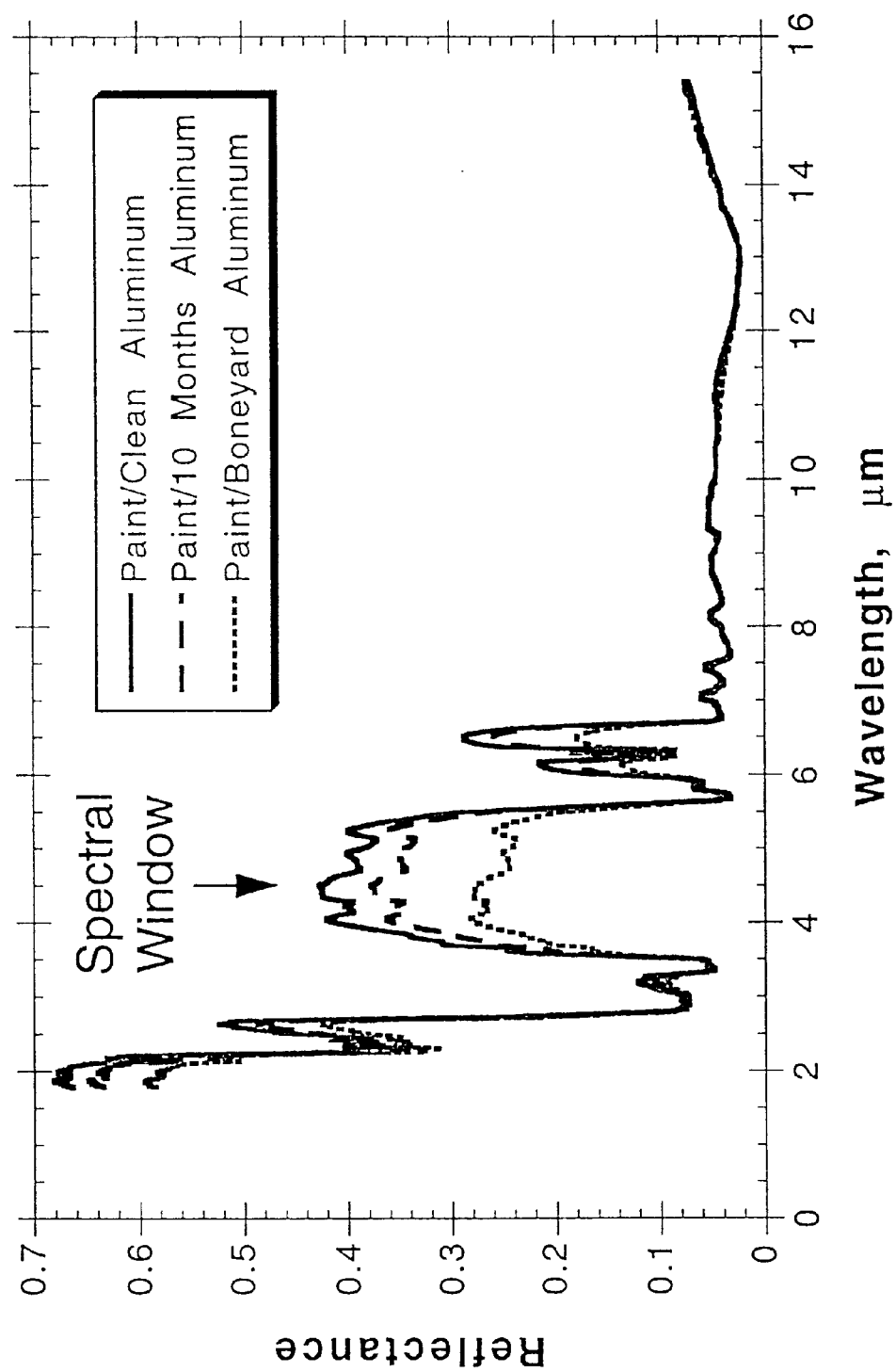
FIG. 2 is a illustrative data chart plotting reflectance as function of wavelength for coated substrates with the substrates having varying surface characteristics.
Figure 3:
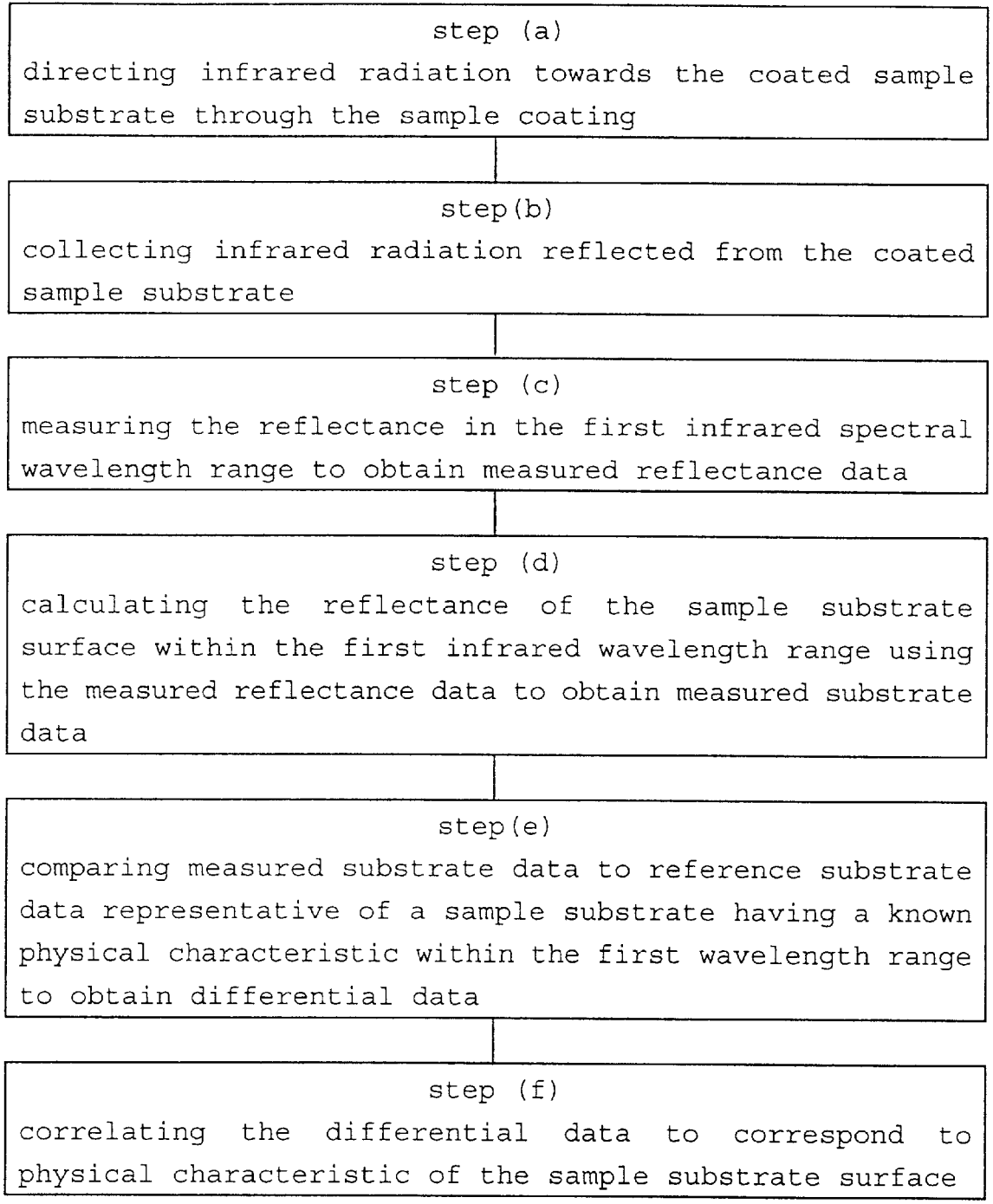
FIG. 3 is a flow chart of another embodiment of the method of the present invention.

Referring now to the drawings wherein the showings are for purposes of illustrating a preferred embodiment of the present invention only, and not for purposes of limiting the same, FIGS. 1–3 illustrate a method for evaluating substrate surfaces of coated substrates which is constructed in accordance with the present invention.

In accordance with the present invention, there is provided a spectral nondestructive method for evaluating substrate surface characteristics of a sample substrate having sample substrate surface and a visually opaque sample coating disposed on the sample substrate surface. In this respect, the sample coating is generally nontransmissive in the visible light wavelength range. The sample coating has a sample coating surface. The sample coating is further characterized as being transmissive within a first infrared spectral wavelength range. Preferably, the transmittance of the sample coating is greater than fifty percent. In the preferred embodiment, the infrared spectral wavelength range is in the infrared region between 2 (two) and 7 (seven) microns in length. It is contemplated that while the coating may be opaque (and therefore having a very low transmittance) for wavelengths within the visual spectrum, the sample coating has a greater transmittance within the first infrared spectral wavelength range. In this respect, the first infrared spectral wavelength range provides an infrared "window" through which infrared radiation may pass.

The sample coating may take the form of paint which is designed to be visually opaque. It is contemplated that the sample coating may be formed of virtually any material which has an infrared "window" and may include oil-based paint, water-thinned paint, varnish, enamel, lacquer and other polymer media. The sample substrate may be any material which is characterized by a reflectance signature within the first infrared spectral wavelength range. Thus, the sample coated substrate may be a composite which forms the exterior skin of an aircraft or steel as is used for bridges.

Referring now to the flowchart of steps of FIG. 1, the method begins with directing infrared radiation from an infrared radiation source towards the coated sample substrate. Preferably, a collimated beam of infrared light is provided incident upon the coated sample substrate at a desired evaluation location. Specular and diffuse infrared radiation reflected from the coated sample substrate is collected. A hemispherical integrating sphere may be coupled to a Fourier transform infrared (FTIR) spectrometer for this purpose. In such a configuration the integrating sphere typically is provided with an incident beam port and a specimen port. An infrared beam is directed through the incident beam port, through the specimen port and onto the evaluation location of the sample substrate. The integrating sphere is adapted to capture all of the reflected energy, spectral and diffuse, within the first infrared spectral wavelength range. The integrating sphere is further provided with an exit port which terminates in a photodetector. The photodetector facilitates reflectance measurements, in terms of intensity, as a function of wavelength. The collimated radiation beam may be electromagnetic energy of any wavelength, as long as the energy wavelength is within the operating range of the spectrometer. One of ordinary skill in the art will appreciate that the coupling of the integrating sphere to a FTIR spectrometer facilitates rapid measurements of spectra with a high signal to noise ratio. In addition, the present method contemplates utilizing portable devices for collecting and measuring the reflected radiation.

The incident infrared radiation within the first infrared spectral wavelength range passes through (transmitted) the sample coating, reflects off of the sample substrate surface, and back through the sample coating for collection. A portion of the incident radiation is absorbed by the sample substrate surface and therefore defines the reflectance signature of the sample substrate surface. In this respect, reflectance for a given sample may be plotted as a function of wavelength. The shape of the curve is denoted as the reflectance signature for the particular sample.

As such, where the sample coating is opaque or nontransmittal for a given wavelength, the collected radiation represents the reflectance of the sample coating only. Thus, where a substrate coating is formed of a thick metallic material the transmittance is essentially zero and any collected radiation represents radiation which is reflected. Importantly, it is recognized that where the sample coating is transmittal for a given wavelength range (e.g., the first infrared spectral wavelength range) a component of the reflected radiation is representative of the underlying sample substrate surface. In this regard, where the sample substrate is formed of a highly reflective material, such as aluminum and the coating is formed of a thin layer of simple organic paint, a component of the collected infrared radiation represents the spectral signature of the underlying aluminum substrate. As one of ordinary skill in the art will recognize, it is desirable that the transmittance within the first infrared spectral wavelength range or infrared window be relatively high and be preferably greater than fifty percent. Such transmittance is contemplated to be a function of material type and thickness.

Having collected and measured the reflected infrared radiation to obtain measured reflectance data, such data is compared to reference reflectance data within the first infrared spectral wavelength range. The reference reflectance data is representative of a sample substrate surface having a known physical characteristic. Such comparison produces differential data. The differential data is correlated to correspond to physical characteristics of the sample substrate surface.

For example, the reference reflectance data may represent collected and measured reflectance data for the identical sample as measured upon completion of manufacture. Presumably, at such a time, the sample exists in a desired physical state. Upon exposure to various environmental conditions, however, the sample substrate surface may become corroded. Because the sample substrate surface is coated with a visibly opaque coating, visual inspection of the underlying substrate surface conditions (e.g., the existence and extent of corrosion) is not feasible. It is recognized, however, that spectral reflectance can be used to obtain chemical and physical information, and therefore evaluate the condition, of materials by using characteristic infrared spectral signatures in the reflectance spectrum. It is recognized that many materials, including organics (e.g., paints and composites) and metallic (e.g., aluminum, steel) have characteristic spectral reflectance that change as their surface condition changes due to factors such as corrosion and heat. The reflectance from many of these material have a significant diffuse component, especially corrosion products such as rust. As such, the measured reflectance data facilitates such evaluation of the surface conditions of the underlying sample substrate surface. Thus, the identified physical characteristics or changes may correspond to corrosion, heat damage, and any other physical or chemical phenomenon which result in a change in the reflectance characteristics of the substrate surface. As such, it is contemplated that the reference reflectance data and differential data may be gathered, empirically or otherwise, and stored in a historical data base for future reference.

Referring now to FIG. 2, there is depicted reflectance data of a painted aluminum panel as plotted as a function of wavelength within the infrared spectrum. The Y-axis represents the measured spectral reflectance. The uppermost curve corresponds to the panel in a painted "clean" (i.e., no corrosion) state and therefore has a relatively higher reflectance within the spectaral window of interest. The intermediate data curve is associated with the painted aluminum panel after it was weathered for ten months. While the panel visually appeared to be uncorroded, the data shows otherwise. As can be seen, within a wavelength range of two to seven microns (the first spectral wavelength range), there is a definite deviation between the two data curves. Such deviation is the result of the development of aluminum substrate surface corrosion which directly impacts the reflectance/absorption signature of the underlying aluminum material. The lowermost curve corresponds the panel after being severely environmentally exposed or in a "boneyard" condition. A pronounced deviation between this curve and the others is observed within the first wavelength range. This is due to the increased absorption associated with increased corrosion of the panel.

Accordingly, the method of the present invention facilitates a nondestructive, non-contact evaluation technique of coated substrate surfaces. While the data present in FIG. 2 illustrates chemical changes of an aluminum panel as a result of corrosion, it is contemplated that any physical/chemical change (with a corresponding change in reflectance signature) of the underlying substrate surface may be evaluated.

In addition, the method of the present evaluation technique may further include a system calibration procedure in which reflected infrared radiation is measured and collected in a second infrared spectral wavelength range to obtain measured calibration reflectance data. The average transmittance of the sample coating in the first infrared spectral wavelength range being greater than the average transmittance in the second infrared spectral wavelength range. The transmittance of the coating on the second infrared spectral window is essentially zero. In this regard, the reflectance data of the second infrared spectral wavelength range is associated with the coating and not the underlying substrate. Such measured calibration data is compared to reference calibration data within the second infrared spectral wavelength range. In this respect, where the transmittance of the coating is essentially zero within the second infrared spectral wavelength range any deviations between the compared data represents physical/chemical changes or characteristics of the coating itself rather than the underlying substrate.

Referring now to flowchart of step illustrated in FIG. 3, there is provided an alternative embodiment of the present invention. As described above a suitable device is configured to provide incident infrared radiation on the coated sample substrate through the sample coating. In addition, as described above, specular and diffuse reflected infrared radiation is collected and measured from the coated sample substrate to obtain measured reflectance data within a first infrared spectral wavelength range. Importantly, the reflectance of the sample substrate surface within the first infrared wavelength range using the measured reflectance data is calculated to obtain measured substrate data. This calculation uses the optical properties of the coating, which can be measured or obtained from literature. The measured substrate data is then compared to reference substrate data within the first infrared wavelength range to obtain differential data. The differential data is identified to correspond to physical changes of the sample substrate surface. Preferably, the reference substrate data is representative of a reference substrate formed of similar material as that of the sample substrate. Thus, it is understood that the reference substrate data is associated with a bare or uncoated substrate. In this respect, this alternative embodiment of the present method of the present invention may have particular application where suitable reference data corresponding to a coated substrate is unavailable.

Additional modifications and improvements of the present invention may also be apparent to those of ordinary skill in the art. Thus, the particular combination of parts described and illustrated herein is intended to represent only one embodiment of the present invention, and is not intended to serve as limitations of alternative devices within the spirit and scope of the invention.

What is claimed is:

1. A spectral nondestructive method for evaluating substrate surface characteristics of a sample substrate having a sample substrate surface and a generally visually nontransmissive sample coating disposed on the sample substrate surface, the sample coating being transmissive within a first infrared spectral wavelength range, the sample substrate being reflective within the first infrared spectral wavelength range, the method comprising the steps of:

(a) directing infrared radiation having a wavelength within the first infrared spectral wavelength range from an infrared radiation source towards the coated sample substrate through the sample coating disposed thereon;

(b) collecting specular and diffuse infrared radiation reflected from the coated sample substrate through the sample coating disposed thereon;

(c) measuring the reflected radiation as a function of wavelength in the first infrared spectral wavelength range to obtain measured reflectance data representative of the reflectance of the coated sample substrate;

(d) comparing the measured reflectance data to reference reflectance data representative of a sample substrate surface having a known physical characteristic within the first wavelength range to obtain differential data; and (e) correlating the differential data to physical characteristics of the sample substrate surface.

2. The method of claim 1 wherein the first infrared spectral wavelength range being from 2 to 7 microns.

3. The method of claim 1 wherein step (a) comprises directing a collimated infrared light beam.

4. The method of claim 3 wherein the reflected infrared radiation is collected in an integrating sphere.

5. The method of claim 1 wherein step (c) comprises measuring the reflectance of the coated sample substrate using a spectrometer.

6. The method of claim 5 wherein the spectrometer is a Fourier transform infrared spectrometer.

7. The method of claim 1 wherein the reflectance of the coated sample substrate is measured using a portable device.

8. The method of claim 1 wherein the reference reflectance data being representative of a reference substrate having a reference coating disposed thereon, the reference substrate and coating being formed of similar material as that of the sample substrate and coating.

9. The method of claim 1 wherein step (c) further comprises measuring the reflected radiation of the coated sample substrate as a function of wavelength in a second infrared spectral wavelength range to obtain measured calibration reflectance data and step (d) further comprises comparing the measured calibration data to reference calibration data within the second infrared spectral wavelength range, the average transmittance of the sample coating in the first infrared spectral wavelength range being greater than the average transmittance in the second infrared spectral wavelength range.

10. The method of claim 1 wherein the physical characteristics of the sample substrate surface correspond to corrosion.

11. The method of claim 1 wherein the physical characteristics of the sample substrate surface correspond to heat damage.

12. A spectral nondestructive method for evaluating substrate surface characteristics of a sample substrate having a sample substrate surface and a generally visually nontransmissive sample coating disposed on the sample substrate surface, the sample coating being transmissive within a first infrared spectral wavelength range, the sample substrate being reflective within the first infrared spectral wavelength range, the method comprising the steps of:

(a) directing infrared radiation having a wavelength within the first infrared spectral wavelength range from an infrared radiation source towards the coated sample substrate through the sample coating disposed thereon;

(b) collecting specular and diffuse infrared radiation reflected from the coated sample substrate through the sample coating disposed thereon;

(c) measuring the reflected radiation as a function of wavelength in the first infrared spectral wavelength range to obtain measured reflectance data to obtain measured substrate data;

(d) calculating the reflectance of the sample substrate surface within the first infrared wavelength range using the measured reflectance data to obtain measured substrate data;

(e) comparing measured substrate data to reference substrate data representative of a sample substrate having a known physical characteristic within the first wavelength range to obtain differential data; and (f) correlating the differential data to correspond to physical characteristic of the sample substrate surface.

13. The method of claim 12 wherein the first infrared spectral wavelength range being from 2 to 7 microns.

14. The method of claim 12 wherein step (a) comprises directing a collimated infrared light beam.

15. The method of claim 12 wherein the reflected infrared radiation is collected in an integrating sphere.

16. The method of claim 12 wherein step (c) comprises measuring the reflectance of the coated sample substrate using a spectrometer.

17. The method of claim 16 wherein the spectrometer is a Fourier transform infrared spectrometer.

18. The method of claim 12 wherein the reflectance of the coated sample substrate is measured using a portable device.

19. The method of claim 12 wherein the reference substrate data being representative of a reference substrate formed of similar material as that of the sample substrate.

20. The method of claim 12 wherein the physical characteristics of the sample substrate surface correspond to corrosion.

21. The method of claim 12 wherein the physical characteristics of the sample substrate surface correspond to heat damage.

22. A spectral nondestructive method for evaluating substrate surface characteristics of a substrate surface having a generally visually nontransmissive coating disposed thereon, the coating being transmissive within a first infrared spectral wavelength range, the substrate surface being reflective within the first infrared spectral wavelength range, the method comprising the steps of:

(a) directing infrared radiation having a wavelength within the first infrared spectral wavelength range from an infrared source towards the coated substrate surface through the coating disposed thereon;

(b) collecting specular and diffuse infrared radiation reflected from the coated substrate surface through the coating disposed thereon; and (c) evaluating the reflected infrared radiation to determine the substrate surface characteristics.

23. The method of claim 22 wherein step (c) comprises the steps of:

(a) measuring the reflected radiation as a function of wavelength in the first infrared spectral wavelength range to obtain measured reflectance data representative of the reflectance of the coated substrate surface;

(b) comparing the measured reflectance data to reference reflectance data representative of a substrate surface having a known physical characteristic within the first wavelength range to obtain differential data; and (c) correlating the differential data to physical characteristics of the substrate surface.

* * * * *